United States Patent

Hoeffkes et al.

[11] Patent Number: 6,090,161
[45] Date of Patent: *Jul. 18, 2000

[54] COLORANTS FOR KERATIN FIBERS COMPRISING A 5,6-DIHYDROXYINDOLINE DERIVATIVE AND A SECONDARY INTERMEDIATE

[75] Inventors: Horst Hoeffkes; Dieter Schrader, both of Duesseldorf, Germany; Hiroshi Tanaka, Saitama Prefecture, Japan

[73] Assignee: Henkel Kommanditgesellschaft Auf Aktien (KGaA), Duesseldorf, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 09/127,422

[22] Filed: Jul. 31, 1998

[30] Foreign Application Priority Data

Jul. 31, 1997 [DE] Germany ............... 197 32 975

[51] Int. Cl.$^7$ ................................. A61K 7/13
[52] U.S. Cl. ........................ 8/409; 8/408; 8/423
[58] Field of Search ............... 8/405, 406, 408, 8/409, 423, 574

[56] References Cited

U.S. PATENT DOCUMENTS

| | | | |
|---|---|---|---|
| 4,013,494 | 3/1977 | Parent et al. | 8/423 |
| 4,865,774 | 9/1989 | Fabry et al. | 510/428 |
| 4,931,218 | 6/1990 | Schenker et al. | 510/498 |
| 5,034,015 | 7/1991 | Junino et al. | 8/423 |
| 5,178,637 | 1/1993 | Lagrange et al. | 8/423 |
| 5,180,396 | 1/1993 | Grollier et al. | 8/405 |
| 5,294,726 | 3/1994 | Behler et al. | 554/98 |
| 5,350,424 | 9/1994 | Shansky | 8/406 |
| 5,413,612 | 5/1995 | Wenke | 8/423 |
| 5,538,517 | 7/1996 | Samain et al. | 8/423 |
| 5,609,650 | 3/1997 | Knuebel et al. | 8/423 |
| 5,792,220 | 8/1998 | Wenke et al. | 8/423 |

FOREIGN PATENT DOCUMENTS

| | | |
|---|---|---|
| 0 462 857 | 12/1991 | European Pat. Off. |
| 0 530 229 | 3/1993 | European Pat. Off. |
| 0 593 038 | 4/1994 | European Pat. Off. |
| 0 613 366 | 9/1994 | European Pat. Off. |
| 613366 | 9/1994 | European Pat. Off. |
| 2 636 235 | 9/1989 | France . |
| 37 23 354 | 1/1989 | Germany . |
| 37 25 030 | 2/1989 | Germany . |
| 39 26 344 | 8/1989 | Germany . |
| 2 211 517 | 7/1989 | United Kingdom . |

OTHER PUBLICATIONS

The Science of Hair Care, Chap. 7 pp. 235–261 and Chap. 8 pp. 263–286, (1986), No month available.
Derwent Patent Abstract (WPAT) 91–347477/48 of EP 530229, Mar. 1993.
Derwent Patent Abstract (WPAT) 93–176345/22 of EP 613366, Sep. 1994.
Derwent Patent Abstract (WPAT) 89–016906/03 of DE 3723354, Jan. 1989.
Derwent Patent Abstract (WPAT) 89–033330/05 of DE 3725030, Feb. 1989.
Derwent Patent Abstract (WPAT) 91–073475/10 of DE 3926344, Feb. 1991.

*Primary Examiner*—Caroline D. Liott
*Attorney, Agent, or Firm*—Wayne C. Jaeschke; Glenn E.J. Murphy

[57] ABSTRACT

Oxidation colorants which contain at least one secondary intermediate and at least one derivative of 5,6-dihydroxyindoline corresponding to formula (I):

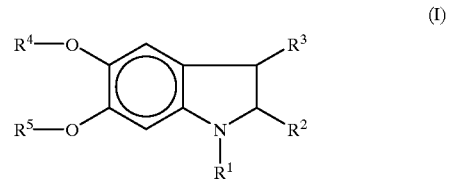

in which—independently of one another—
$R^1$ is hydrogen, a $C_{1-4}$ alkyl group or a $C_{1-4}$ hydroxyalkyl group,
$R^2$ is hydrogen or a —COOH group which may even be present as a salt with a physiologically compatible cation,
$R^3$ is hydrogen or a $C_{1-4}$ alkyl group,
$R^4$ is hydrogen, a $C_{1-4}$ alkyl group or a group —CO—$R^6$ where $R^6$ is a $C_{1-4}$ alkyl group and
$R^5$ is one of the groups mentioned for $R^4$,
or a physiologically compatible salt of these compounds with an organic or inorganic acid in an aqueous carrier and which are free from oxidation dye precursors of the primary intermediate type enable hair to be colored in particular in black tones with no tinges of red. In particular, completely or partly grey hair can be colored in tones which come very close to the color of the hair before greying.

11 Claims, No Drawings

COLORANTS FOR KERATIN FIBERS COMPRISING A 5,6-DIHYDROXYINDOLINE DERIVATIVE AND A SECONDARY INTERMEDIATE

BACKGROUND OF THE INVENTION

This invention relates to oxidation colorants containing special indoline derivatives in combination with secondary intermediates for coloring keratin fibers.

By virtue of their intensive colors and good fastness properties, so-called oxidation colorants play a prominent role in the coloring of keratin fibers, particularly human hair. Oxidation colorants normally contain oxidation dye precursors, so-called primary intermediates and secondary intermediates. The primary intermediates form the actual dyes with one another or by coupling with one or more secondary intermediates in the presence of oxidizing agents or atmospheric oxygen.

Good oxidation dye precursors are expected to satisfy above all the following requirements: they must form the required color tones with sufficient intensity and fastness during the oxidative coupling reaction. In addition, they must be readily absorbed onto the fibers with no significant differences—particularly in the case of human hair—between damaged and freshly regrown hair (leveling behavior). They must be resistant to light, heat and the effect of chemical reducing agents, for example permanent wave lotions. Finally, if they are used to color hair, they should not overly stain the scalp and, above all, should be toxicologically and dermatologically safe.

The primary intermediates used are, for example, primary aromatic amines containing another free or substituted hydroxy or amino group in the para position or the ortho position, diaminopyridine derivatives, heterocyclic hydrazones, 4-aminopyrazolone derivatives and 2,4,5,6-tetraaminopyrimidine and derivatives thereof.

Special representatives are inter alia p-toluylenediamine, p-aminophenol, N,N-bis-(2-hydroxyethyl)-p-phenylenediamine, 2-(2,5-diaminophenoxy)-ethanol, 1-phenyl-3-carboxyamido4-amino-5-pyrazolone and 4-amino-3-methylphenol and 2,4,5,6-tetraaminopyrimidine.

The secondary intermediates are generally m-phenylenediamine derivatives, naphthols, resorcinol and resorcinol derivatives, pyrazolones, m-aminophenols and pyridine derivatives. Particularly suitable secondary intermediates are 1-naphthol, pyrogallol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 2,4-diaminophenoxyethanol, 1,3-bis-(2,4-diaminophenoxy)-propane, 2-chlororesorcinol, 2-chloro-6-methyl-3-aminophenol, 2-methyl resorcinol, 2,6-dihydroxypyridine, 2-aminomethyl-3-amino-6-methoxypyridine and 2,6-diaminopyridine.

With regard to the dyes suitable for use in the hair coloring and tinting formulations according to the invention, reference is also specifically made to Ch. Zviak's work The Science of Hair Care, Chapter 7 (pages 248–250; Substantive Dyes) and Chapter 8, pages 264–267; Oxidation Dye Precursors), published as Vol. 7 of the Series "Dermatology" (Editors: Ch. Culnan and H. Maibach), Marcel Dekker Inc., New York/Basel, 1986 and to the "Europäische Inventar der Kosmetik-Rohstoffe" published by the Europäische Gemeinschaft and available in diskette form from the Bundesverband Deutscher Industrie- und Handelsunternehmen für Arzneimittel, Reformwaren und Körperpflegemittel e. V., Mannheim, Germany.

In general, natural color tones cannot be obtained with a single secondary intermediate/primary intermediate combination. In practice, therefore, a combination of various primary intermediates and secondary intermediates has to be used to obtain a natural-looking color. So-called substantive dyes may also be required to adjust the particular color tone required.

Accordingly, there is a constant need for new improved colorants.

In recent years, corresponding investigations have shown indoline derivatives to be suitable, particularly for hair colorants. Thus, EP-B1-0 530 229 describes the use of 5,6-dihydroxyindoline derivatives as secondary intermediates in oxidation colorants. This document discloses colorants which, besides the indolines, contain typical primary intermediates and/or substantive dyes. Colorants additionally containing typical secondary intermediates are not mentioned in this document. EP-B1-0 613 366 relates to the use of the same 5,6-dihydroxyindoline derivatives for improving the coloring properties of formulations based on substantive dyes or on oxidation dye precursors of the secondary intermediate and primary intermediate type. The combination of these 5,6-dihydroxyindolines with oxidation dye precursors of the secondary intermediate type alone is not mentioned in this document.

DESCRIPTION OF THE INVENTION

It has now been found that excellent colors having outstanding fastness properties can surprisingly be obtained with oxidation colorants which contain these 5,6-dihydroxyindoline derivatives in combination with typical secondary intermediates as dye precursors. Surprisingly, various colors which are free from red components are also obtained. Colors such as these which are of interest above all for dark to black hair can only be verified with considerable difficulty where known secondary intermediate/primary intermediate combinations are used. In particular, it is possible in accordance with the invention to restore partly or completely grey hair to its original natural color in such a way that no significant difference from any naturally pigmented hair still present is visible. The color tones described by the expert as "flat" are of particular significance in this regard.

Accordingly, the present invention relates to oxidation colorants for coloring keratin fibers, more particularly human hair, containing at least one secondary intermediate in an aqueous carrier, characterized in that they contain (a) at least one derivative of 5,6-dihydroxyindoline corresponding to formula (I):

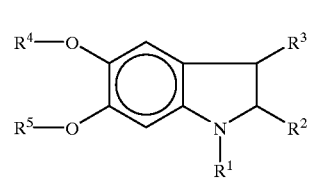

(I)

in which—independently of one another—

$R^1$ is hydrogen, a $C_{1-4}$ alkyl group or a $C_{1-4}$ hydroxyalkyl group, $R^2$ is hydrogen or a —COOH group which may even be present as a salt with a physiologically compatible cation, $R^3$ is hydrogen or a $C_{1-4}$ alkyl group, $R^4$ is hydrogen, a $C_{1-4}$ alkyl group or a group —CO—$R^6$ where $R^6$ is a $C_{1-4}$ alkyl group and $R^5$ is one of the groups mentioned for $R^4$, or a physiologically compatible salt of these compounds with an organic or inorganic acid, and (b) are free from oxidation dye precursors of the primary intermediate type.

In the context of the invention, keratin fibers are understood to include pelts, wool, feathers and, in particular, human hair. Although the oxidation colorants according to the invention are particularly suitable for coloring keratin fibers, there are no basic obstacles to their use in other fields, particularly in color photography.

The colorants according to the invention contain derivatives of 5,6-dihydroxyindoline corresponding to formula (I) as a first compulsory component. According to the invention, suitable representatives are, for example, 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline. Preferred derivatives are N-methyl-5,6-dihydroxyindoline and, in particular, 5,6-dihydroxyindoline.

The compounds of formula (I) present in the hair colorants according to the invention may be used both as free bases and in the form of their physiologically compatible salts with inorganic or organic acids, for example in the form of hydrochlorides, sulfates and hydrobromides.

The colorants according to the invention contain a secondary intermediate as a second compulsory component.

According to the invention, suitable secondary intermediates are, for example, 1-naphthol, pyrogallol, 1,5-, 2,7- and 1,7-dihydroxynaphthalene, o-aminophenol, 5-amino-2-methylphenol, m-aminophenol, resorcinol, resorcinol monomethyl ether, m-phenylenediamine, 1-phenyl-3-methyl-5-pyrazolone, 2,4dichloro-3-aminophenol, 1,3-bis-(2,4-diaminophenoxy)-propane, 4-chlororesorcinol, 2-chloro-6-methyl-3-aminophenol, 2-methyl resorcinol, 5-methyl resorcinol, 2,5-dimethyl resorcinol, 2,6-dihydroxypyridine, 2,6-diaminopyridine, 2-amino-3-hydroxypyridine, 2,6-dihydroxy-3,4-diaminopyridine, 3-amino-2-methylamino-6-methoxypyridine, 4-amino-2-hydroxytoluene, 2,6-bis-(2-hydroxyethylamino)-toluene, 2,4-diaminophenoxyethanol, 1-methoxy-2-amino-4-(2-hydroxyethylamino)-benzene, 2-methyl-4-chloro-5-aminophenol, 6-methyl-1,2,3,4-tetrahydroquinoxaline, 3,4-methylenedioxyphenol, 3,4-methylenedioxyaniline, 2,6-dimethyl-3-aminophenol, 3-amino-6-methoxy-2-methylaminophenol, 2-hydroxy4-aminophenoxyethanol, 2-methyl-5-(2-hydroxyethylamino)-phenol and 2,6-dihydroxy-3,4-dimethyl pyridine.

Preferred secondary intermediates are 1-naphthol, pyrogallol, 1,5-, 2,7- and 1,7-dihydroxynaphthalene, 5-amino-2-methylphenol, 5-amino-2-methyl-4-chlorophenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diaminophenoxy)-propane, 4-chlororesorcinol, 2-chloro-6-methyl-3-aminophenol, 2-methyl resorcinol, 5-methyl resorcinol, 2,6-dihydroxypyridine, 2,6-diaminopyridine, 2,4-diaminophenoxyethanol, 2-chloro-6-methyl-3-aminophenol and physiologically compatible salts thereof.

Particularly preferred secondary intermediates are 2,4-diaminophenoxyethanol, resorcinol, 2-methyl resorcinol, 2,5-dimethyl resorcinol, 4-chlororesorcinol, 5-amino-2-methylphenol, 5-amino-2-methyl-4-chlorophenol, m-aminophenol, 1-naphthol, 2,7-dihydroxynaphthalene and physiologically compatible salts thereof.

The colorants according to the invention may of course also contain more than one secondary intermediate. Preferred secondary intermediate combinations are 2,4-diaminophenoxyethanol/1,3-bis-(2,4-diaminophenoxy)-propane 2,4-diaminophenoxyethanol/resorcinol 2,4-diaminophenoxyethanol/2-methylresorcinol 2,4-diaminophenoxyethanol/5-methyl resorcinol 2,4-diaminophenoxyethanol/4-chlororesorcinol 2,4-diaminophenoxyethanol/resorcinol monomethylether 2,4-diaminophenoxyethanol/resorcinol/2-methylresorcinol 2,4-diaminophenoxyethanol/resorcinol/5-methylresorcinol 2,4-diaminophenoxyethanol/resorcinol/4-chlororesorcinol 2,4-diaminophenoxyethanol/resorcinol monomethylether/4-chlororesorcinol 2,4-diaminophenoxyethanol/resorcinol monomethylether/2-methylresorcinol 2,4-diaminophenoxyethanol/resorcinol monomethylether/5-methylresorcinol 2,4-diaminophenoxyethanol/2-methylamino-3-amino-6-methoxypyridine 2,4-diaminophenoxyethanol/2,6-dimethoxy-3,5-diaminopyridine 2,4-diaminophenoxyethanol/5-amino-2-methylphenol 1,3-bis-(2,4-diaminophenoxy)-propane/resorcinol 1,3-bis-(2,4-diaminophenoxy)-propane/2-methylrecorcinol 1,3-bis-(2,4-diaminophenoxy)-propane/5-methylresorcinol 1,3-bis-(2,4-diaminophenoxy)-propane/4-chlororesorcinol 1,3-bis-(2,4-diaminophenoxy)-propane/resorcinol monomethylether 1,3-bis-(2,4-diaminophenoxy)-propane/2-methylamino-3-amino-6-methoxypyridine 1,3-bis-(2,4-diaminophenoxy)-propane/2,6-dimethoxy-3,5-diaminopyridine 1,3-bis-(2,4-diaminophenoxy)-propane/5-amino-2-methylphenol 2-methylamino-3-amino-6-methoxypyridine/2,6-dimethoxy-3,5-diaminopyridine 2-methylamino-3-amino-6-methoxypyridine/resorcinol 2-methylamino-3-amino-6-methoxypyridine/2-methylresorcino 2-methylamino-3-amino-6-methoxypyridine/5-methylresorcinol 2-methylamino-3-amino-6-methoxypyridine/4-chlororesorcinol 2-methylamino-3-amino-6-methoxypyridine/resorcinol monomethylether 2-methylamino-3-amino-6-methoxypyridine/5-amino-2-methylphenol 2,6-dimethoxy-3,5-diaminopyridine/resorcinol 2,6-dimethoxy-3,5-diaminopyridine/2-methylresorcinol 2,6-dimethoxy-3,5-diaminopyridine/5-methylresorcinol 2,6-dimethoxy-3,5-diaminopyridine/4-chlororesorcinol 2,6-dimethoxy-3,5-diaminopyridine/resorcinol monomethylether 2,6-dimethoxy-3,5-diaminopyridine/5-amino-2-methylphenol 5-amino-2-methylphenol/resorcinol 5-amino-2-methylphenol/2-methylresorcinol 5-amino-2-methylphenol/5-methylresorcinol 5-amino-2-methylphenol/4-chlororesorcinol 5-amino-2-methylphenol/resorcinol monomethylether A combination of resorcinol with 2,4-diaminophenoxyethanol is a preferred secondary intermediate combination.

The oxidation colorants according to the invention contain the compound of formula (I) in quantities of typically 0.05 to 10% by weight and preferably 0.2 to 5% by weight and the secondary intermediates in quantities of 0.01 to 20% by weight and preferably 0.2 to 5% by weight, based on the oxidation colorant as a whole.

According to the invention, the colorants preferably contain no other dyes or dye precursors apart from the 5,6-dihydroxyindoline derivatives corresponding to formula (I) and the secondary intermediates. However, this does not rule out the additional presence of substantive dyes in small amounts in the colorants according to the invention, particularly for slight adjustments of color tone. Substantive dyes are typically nitrophenylenediamines, nitroaminophenols, azo dyes, anthraquinones or indophenols. Preferred substantive dyes are the compounds known under the International names or commercial names of HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17 and also 4-amino-2-nitrodiphenylamine-2'-carboxylic acid, 6-nitro-1,2,3,4-tetrahydroquinoxaline, hydroxyethyl-2-nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene. Among these substantive dyes, compounds which give blue color tones are preferred. In this embodiment, the colorants according to the invention preferably contain the substantive dyes in a quantity of more than 0.01% by weight, based on the colorant as a whole.

In addition, the colorants according to the invention may also contain naturally occurring dyes such as, for example, henna red, henna neutral, henna black, camomile blossom, sandalwood, black tea, green tea, black alder bark, sage, logwood, madder root, catechu, sedre and alkanet. Products containing tannins, such as henna neutral and green tea, are preferred.

The 5,6-dihydroxyindoline derivatives, the secondary intermediates and the substantive dyes optionally present do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

To produce the colorants according to the invention, the oxidation dye precursors are incorporated in a suitable water-containing carrier. For coloring hair, such carriers are, for example, cremes, emulsions, gels or even surfactant-containing foaming solutions, for example shampoos, foam aerosols or other formulations suitable for application to the hair.

The hair colorants according to the invention are adjusted to a pH value of preferably 6.5 to 11.5 and, more preferably, 9 to 10.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants. Anionic surfactants can be particularly useful.

Suitable anionic surfactants for the hair colorants according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ether, amide and hydroxyl groups and—generally—ester groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear and branched fatty acids containing 8 to 22 carbon atoms (soaps), ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O(CH$_2$—CH$_2$O)$_x$—SO$_3$H, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one —COO$^{(-)}$ or —SO$_3$$^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a $C_{8-18}$ alkyl or acyl group, contain at least one free amino group and at least one —COOH or —$SO_3H$ group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and $C_{12-18}$ acyl sarcosine.

Nonionic surfactants contain, for example, a polyol group, a polyalkylene glycol ether group or a combination of polyol and polyglycol ether groups as the hydrophilic group. Examples of such compounds are products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group, $C_{12-22}$ fatty acid monoesters and diesters of products of the addition of 1 to 30 moles of ethylene oxide to glycerol, $C_{8-22}$ alkyl mono- and oligoglycosides and ethoxylated analogs thereof, products of the addition of 5 to 60 moles of ethylene oxide to castor oil and hydrogenated castor oil, products of the addition of ethylene oxide to sorbitan fatty acid esters, products of the addition of ethylene oxide to fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as Amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, cationic polymers, such as quaternized cellulose ethers, polysiloxanes containing quaternary groups, dimethyl diallyl ammonium chloride polymers, acrylamideldimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol, zwitterionic and amphoteric polymers such as, for example, acrylamidopropyl/trimethyl ammonium chloride/acrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, carob bean flour, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as glucose, maleic acid and lactic acid, hair-conditioning compounds, such as phospholipids, for example soya lecithin, egg lecithin and kephalins, and also silicone oils, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solubilizers, such as ethanol, isopropanol, ethylene glycol, propylene glycol, glycerol and diethylene glycol, antidandruff agents, such as Piroctone Olamine and Zinc Omadine, alkalizing agents such as, for example, ammonia, monoethanolamine, 2-amino-2-methylpropanol, 2-amino-2-methylpropane-1,3-diol, triethanolamine, alkali metal and alkaline earth metal hydroxides.

other substances for adjusting the pH value, active substances, such as panthenol, pantothenic acid, allantoin, pyrrolidone carboxylic acids and salts thereof, plant extracts and vitamins, cholesterol, UV absorbers, consistency promoters such as sugar esters, polyol esters or polyol alkyl ethers, fats and waxes, such as spermaceti, beeswax, moritan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates opacifiers, such as latex, pearlescers, such as ethylene glycol mono- and distearate, propellents, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

In a first preferred embodiment, the color is oxidatively developed with atmospheric oxygen alone. To this end, the formulation according to the Invention is applied to the hair, left thereon for preferably 5 to 30 minutes and then rinsed out. If desired, the hair may then be shampooed.

In a second embodiment, a chemical oxidizing agent is additionally used. This is particularly advantageous when human hair is to be not only colored, but also lightened. Particularly suitable oxidizing agents are hydrogen peroxide or addition products thereof with urea, melamine or sodium borate. Oxidation may also be carried out with enzymes. In this case, the enzymes may be used both to produce oxidizing per compounds and to enhance the effect of an oxidizing agent present in small quantities. One example of an enzymatic process is the procedure whereby the effect of small quantities (for example 1% and less, based on the formulation as a whole) of hydrogen peroxide is enhanced by peroxidases. The preparation of the oxidizing agent is preferably mixed with the preparation of the oxidation dye precursors immediately before coloring of the hair. The ready-to-use hair coloring preparation formed should have a pH value in the range from 5 to 11 and preferably in the range from 6 to 10. In a particularly preferred embodiment, the hair colorant is used in a mildly alkaline medium. The application temperatures may be in the range from 15 to 40° C. After a contact time of about 5 to 30 minutes, the hair colorant is removed from the hair to be colored by rinsing. There is no need for the hair to be washed with a shampoo where a carrier of high surfactant content, for example a coloring shampoo, has been used.

In the particular case of hair which is difficult to color, the preparation containing the oxidation dye precursors may be applied to the hair without preliminary mixing with the oxidation component. The oxidation component is applied after a contact time of 5 to 30 and preferably 20 to 30 minutes, optionally after rinsing. After another contact time of 10 to 20 minutes, the hair is rinsed and, if desired, shampooed.

Whichever of the processes mentioned above is used to apply the colorant according to the invention, development of the color may be supported and enhanced by adding certain metal ions to the colorant. Examples of such metal ions are $Zn^{2+}, Cu^{2+}, Fe^{3+}, Mn^{2+}, Mn^{4+}, Li^+, Mg^{2+}, Ca^{2+}$ and $Al^{3+}$. $Zn^{2+}$, $Cu^{2+}$ and $Mn^{2+}$ are particularly suitable. Basically, the metal ions may be used in the form of a physiologically compatible salt. Preferred salts are the acetates, sulfates, halides, lactates and tartrates. Zinc sulfate is a particularly preferred metal salt. Development of the hair color can be accelerated and the color tone can be influenced as required through the use of these metal salts.

It has surprisingly been found that, depending on the oxidation process selected, different coloring results can be obtained with the same colorant.

Accordingly, the present invention also relates to a process for coloring human hair in which one of the above-mentioned colorants according to the invention is applied to the hair and the color is subsequently developed. Development of the color with atmospheric oxygen can be advantageous.

In one particular embodiment of this process, the final color is developed by repeated application of the colorant and subsequent oxidation with air. In this embodiment, the colorant is preferably applied at intervals of about one day. Special color tones can be selectively obtained in this way.

The following Examples are intended to illustrate the invention.

EXAMPLES

1. Color Development

Colorants with the compositions shown in Table 1 below (where the figures shown represent grams, unless otherwise indicated) were initially prepared.

Where the color was developed by oxidation with $H_2O_2$, the colorant was mixed with a 3% hydrogen peroxide preparation in a ratio by weight of 1:1 immediately before application. The application mixture obtained was left on the hair for 30 minutes at room temperature. The hair was then rinsed and dried.

Where the color was developed by oxidation with air, the colorant was left on the hair for 30 minutes at room temperature. The hair was then rinsed and dried.

The colors were developed on natural white hair tresses (Kerling).

TABLE 1

Formulations

| Component | Formulation B1 | Formulation C1 |
|---|---|---|
| • Texapon ® N28[1] | 20.00 | 20.00 |
| • Dehyton ® K[2] | 12.5 | 12.5 |
| • Lorol ® techn.[3] | 2.0 | 2.0 |
| • Hydrenol ® D[4] | 8.5 | 8.5 |
| • Eumulgin ® B 2[5] | 1.5 | 1.5 |
| • 5,6-Dihydroxyindoline hydrobromide | 1.0 | 1.0 |
| • 2,4-Diaminophenoxyethanol | 0.72 | — |
| • Ammonia | <——— to pH 9.5 ———> | |
| • Water | <——— to 100 ———> | |

[1]Sodium lauryl ether sulfate (ca. 28% active substance; CTFA name: Sodium Laureth Sulfate) (HENKEL)
[2]Fatty acid amide derivative of betaine structure with the formula R—$CONH(CH_2)_3N^+(CH_3)_2CH_2COO^-$ (ca. 30% active substance; CTFA name Cocoamidopropyl Betaine) (HENKEL)
[3]$C_{12-18}$ fatty alcohol (HENKEL)
[4]$C_{16-18}$ fatty alcohol (HENKEL)
[5]Cetylstearyl alcohol containing ca. 20 moles EO (CTFA name: Ceteareth-20) (HENKEL)

TABLE 2

Development of colors

| Formulation | Development process | Result |
|---|---|---|
| B1 | Oxidation with air | Flat mid-blond (with no red) |
| C1 | Oxidation with air | Reddish light blond |
| B1 | Oxidation with $H_2O_2$ | Reddish dark blond |
| C1 | Oxidation with $H_2O_2$ | Reddish mid-blond |

Table 3 below shows the results of coloring with colorants corresponding to those of Table 1 containing 2 g of 5,6-dihydroxyindoline hydrobromide and an equimolar quantity of the secondary intermediate mentioned.

TABLE 3

Development of colors

| Secondary intermediate | Development process | Result |
|---|---|---|
| 2,4-Diaminophenoxyethanol | Oxidation with air | Flat dark blond |
| 2,4-Diaminophenoxyethanol | Oxidation with $H_2O_2$ | Chestnut-colored light brown |
| 1,3-Bis-(2,4-diaminophenoxy)-propane | Oxidation with air | Copper-colored mid-blond |
| 1,3-Bis-(2,4-diaminophenoxy)-propane | Oxidation with $H_2O_2$ | Copper-colored dark blond |
| 2-Methylamino-3-amino-6-methoxypyridine | Oxidation with air | Chestnut-colored mid-brown |
| 2-Methylamino-3-amino-6-methoxypyridine | Oxidation with $H_2O_2$ | Flat chestnut-colored dark blond |
| 2,6-Dimethoxy-3,5-diamino-pyridine | Oxidation with air | Chestnut-colored light brown |
| 2,6-Dimethoxy-3,5-diamino-pyridine | Oxidation with $H_2O_2$ | Chestnut-colored mid-brown |
| Resorcinol | Oxidation with air | Flat chestnut-colored mid-brown |
| Resorcinol | Oxidation with $H_2O_2$ | Chestnut-colored mid-brown |
| 5-Amino-2-methylphenol | Oxidation with air | Flat dark blond |
| 5-Amino-2-methylphenol | Oxidation with $H_2O_2$ | Chestnut-colored light brown |

Table 4 below shows the results of coloring with colorants corresponding to those of Table I containing 2 g of 5,6-dihydroxyindoline hydrobromide and an equimolar quantity of the coupler component mentioned. "1×" oxidation with air signifies the single application of a colorant as described above. "3×" oxidation with air means that the colorant was applied three times as described above on three consecutive days.

TABLE 4

Consecutive color developments by oxidation with air

| Secondary intermediate | Development process | Result |
|---|---|---|
| 2,4-Diaminophenoxyethanol | 1× oxidation with air | Flat dark blond |
| 2,4-Diaminophenoxyethanol | 3× oxidation with air | Very flat mid-brown |
| 1,3-Bis-(2,4-diaminophenoxy)-propane | 1× oxidation with air | Copper-colored mid-blond |
| 1,3-Bis-(2,4-diaminophenoxy)-propane | 3× oxidation with air | Slightly reddish light brown |
| 2-methylamino-3-amino-6-methoxypyridine | 1× oxidation with air | Chestnut-colored mid-brown |
| 2-methylamino-3-amino-6-methoxypyridine | 3× oxidation with air | Slightly reddish mid-dark brown |
| Resorcinol | 1× oxidation with air | Flat chestnut-colored mid-brown |
| Resorcinol | 3× oxidation with air | Very flat mid-brown |
| 5-Amino-2-methylphenol | 1× oxidation with air | Flat dark blond |
| 5-Amino-2-methylphenol | 3× oxidation with air | Very flat dark blond with slight tinges of green |

What is claimed is:

1. An oxidation colorant for keratin fibers comprising:
   (a) a secondary intermediate;
   (b) a 5,6-dihydroxyindoline derivative corresponding to formula (I):

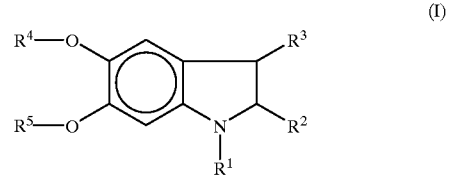

wherein independently of one another
   $R^1$ is hydrogen, a $C_{1-4}$ alkyl group or a $C_{1-4}$ hydroxyalkyl group,
   $R^2$ is hydrogen, a —COOH group, or a —COOH group present as a salt with a physiologically compatible cation,
   $R^3$ is hydrogen or a $C_{1-4}$ alkyl group,
   $R^4$ is hydrogen, a $C_{1-4}$ alkyl group: or a group —CO—$R^6$ where $R^6$ is a $C_{1-4}$ alkyl group, and
   $R^5$ is a group as for $R^4$, or a physiologically compatible salt of said compound of formula (I) with an organic or inorganic acid; and (c) no primary intermediate oxidation dye precursors.

2. An oxidation colorant according to claim 1, wherein the derivative corresponding to formula (I) is selected from the group consisting of 5,6-dihydroxyindoline, N-methyl-5,6-dihydroxyindoline, and physiologically compatible salts thereof.

3. An oxidation colorant according to claim 1, wherein the secondary intermediate is selected from the group consisting of 1-naphthol, pyrogallol, 1,5-dihydroxynaphthalene 2,7-dihydroxynaphthalene, 1,7-dihydroxynaphthalene, 5-amino-2-methylphenol, 5-amino-2-methyl-4-chlorophenol, m-aminophenol, resorcinol, resorcinol monomethyl ether, m-phenylenediamine, 1-phenyl-3- methyl-5-pyrazolone, 2,4-dichloro-3-amino-phenol, 1,3-bis-(2,4-diaminophenoxy)-propane, 4-chlororesorcinol, 2-chloro-6-methyl-3-aminophenol, 2-methyl resorcinol, 5-methyl resorcinol, 2,5-dimethyl resorcinol, 2,6-dihydroxypyridine, 2,6-diaminopyridine, 2,4-diaminophenoxyethanol, and physiologically compatible salts thereof.

4. An oxidation colorant according to claim 3, wherein the secondary intermediate is selected from the group consisting of 2,4-diaminophenoxyethanol, resorcinol, 2-methyl resorcinol, 2,5-dimethyl resorcinol, 4-chlororesorcinol, 5-amino-2-methylphenol, 5amino-2-methyl-4-chlorophenol, m-aminophenol, 2-naphthol, 2,7-dihydroxynaphthalene and physiological compatible salts thereof.

5. An oxidation colorant for keratin fibers, comprising;
   (a) 0.01% to 20% by weight of a secondary intermediate;
   (b) 0.05% to 10% by weight of a 5,6-dihydroxyindoline derivative of formula (I):

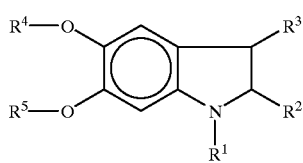

(I)

wherein independently of one another
   $R^1$ is hydrogen, a $C_{1-4}$ alkyl group or a $C_{1-4}$ hydroxyalkyl group,
   $R^2$ is hydrogen, a —COOH group, or a —COOH group present as a salt with a physiologically compatible cation,
   $R^3$ is hydrogen or a $C_{1-4}$ alkyl group,
   $R^4$ is hydrogen, a $C_{1-4}$ alkyl group or a group —CO—$R^6$ where $R^6$ is a $C_{1-4}$ alkyl group, and
   $R^5$ is a group as for $R^4$, or a physiologically compatible salt of said compound of formula (I) with an organic or inorganic acid; and
   (c) no primary intermediate oxidation dye precursors.

6. An oxidation colorant according to claim 5 comprising 0.2% to 5% by weight of the secondary intermediate and 0.2% to 5% by weight of the derivative of formula (I).

7. An oxidation colorant according to claim 5, wherein the derivative of formula (I) is selected from the group consisting of 5,6-dihydroxyindoline, N-methyl-5,6-dihydroxyindoline and physiologically compatible salts thereof.

8. An oxidation colorant according to claim 5, wherein the secondary intermediate is selected from the group consisting of 1-naphthol, pyrogallol, 1,5-dihydronaphthalene, 2,7-dihydroxynapthalene, 1,7-dihydroxynaphthalene, 5-amino-2-methylphenol, 5-amino-2-methyl-4-chlorophenol, m-aminophenol, resorcinol, resorcinol monoethyl ether, m-phenylenediamine, 1-phenyl-3-methyl-5-pyrazolone, 2,4-dichloro-3-amino-phenol, 1,3-bis-(2,4-diaminophenoxy)-propane, 4-chlororesorcinol, 2-chloro-6-methyl-3-aminophenol, 2-methyl resorcinol, 5-methyl resorcinol, 2,5-dimethyl resorcinol, 2,6-dihydroxypyridine, 2,6-diaminopyridine, 2,4-diaminophenoxyethanol, and physiologically compatible salts thereof.

9. An oxidation colorant according to claim 8, wherein secondary intermediate is selected from the group consisting of 2,4-diaminophenoxyethanol, resorcinol, 2-methyl resorcinol, 2,5-dimethyl resorcinol, 4-chlororesorcinol, 5-amino-2-methylphenol, 5-amino-2-methyl-4-chlorophenol, m-aminophenol, 1-naphthol, 2,7-dihydroxynaphthalene and physiologically compatible salts thereof.

10. A method of coloring hair comprising the steps of:
   (a) applying to the hair an oxidation colorant according to claim 1;
   (b) oxidizing the colorant with atmospheric oxygen to develop a color; and
   (c) rinsing the colorant from the hair.

11. A method of coloring hair according to claim 10, wherein steps (a) to (c) are repeated.

* * * * *